United States Patent
Botros et al.

(10) Patent No.: US 7,794,140 B2
(45) Date of Patent: Sep. 14, 2010

(54) METHOD AND SYSTEM FOR MONITORING GAS MIXTURE QUALITY

(75) Inventors: Kamal Botros, Calgary (CA); Steve Hall, Calgary (CA); John Geerligs, Cremona (CA)

(73) Assignee: Transcanada Pipelines Limited, Calgary, Alberta (CA)

( * ) Notice: Subject to any disclaimer, the term of this patent is extended or adjusted under 35 U.S.C. 154(b) by 370 days.

(21) Appl. No.: 12/027,349

(22) Filed: Feb. 7, 2008

(65) Prior Publication Data

US 2009/0201970 A1    Aug. 13, 2009

(51) Int. Cl.
*G01N 25/02* (2006.01)
*G01N 25/56* (2006.01)

(52) U.S. Cl. .................. 374/28; 374/143; 73/25.01; 73/25.04; 73/29.01

(58) Field of Classification Search .............. 374/28, 374/143; 73/25.01, 25.04, 29.01
See application file for complete search history.

(56) References Cited

U.S. PATENT DOCUMENTS 3,487,692 A * 1/1970 Cook, Jr. ............... 73/863.11
4,296,637 A * 10/1981 Calamur et al. ......... 73/863.11

* cited by examiner

*Primary Examiner*—Lisa M Caputo
*Assistant Examiner*—Mirellys Jagan
(74) *Attorney, Agent, or Firm*—Ogilvy Renault LLP

(57) ABSTRACT

A method and system for monitoring the quality of a given gas mixture being transmitted under pressure by throttling a sample of the gas mixture to a representative pressure and measuring the hydrocarbon dew point of the sample at the representative pressure. The measured hydrocarbon dew point is indicative of the cricondentherm of the gas mixture. The representative pressure is pre-selected to provide a pre-selected margin of error between measured hydrocarbon dew points of a set of representative gas mixtures at the representative pressure and respective cricondentherms of the set of representative gas mixtures.

25 Claims, 4 Drawing Sheets

METHOD AND SYSTEM FOR MONITORING GAS MIXTURE QUALITY

FIELD OF THE INVENTION

The present invention relates to a method and system for monitoring gas mixture quality. In particular, the present invention relates to a method and system for monitoring gas mixture quality which can be used when the gas is in the dense-phase region.

BACKGROUND OF THE INVENTION

Operation of natural gas (NG) pipelines at high pressures in the dense-phase region is becoming attractive due to findings of NG fields in harsh environments and in remote areas, such as in Alaska and in the Northern Territories of Canada, where the transportation costs of a conventional pipeline may be prohibitive. The dense-phase is defined as the region where the gas pressure is higher than the cricondenbar. The cricondenbar is the maximum pressure at which two phases such as liquid and gas can coexist. Operation in the dense-phase region offers a means to reduce overall transmission cost and hence encourage the building of new systems in remote and harsh areas. Operating pipelines in the dense-phase permits transportation of raw gases, which typically contain varying amounts of natural gas liquids (NGL) from heavier gas components.

A challenge of dense-phase transportation of gas is related to gas quality monitoring at remote locations. It has been suggested that one of the main specifications of the gas mixture quality in the dense-phase is its cricondentherm. The cricondentherm is defined as the warmest temperature at which a liquid may be formed in a gas mixture. In a general sense, warmer cricondentherms may indicate the presence of heavier gas components which may be of concern from a liquid dropout perspective. Liquid dropout along a pipeline results in not only a loss of a gas component, but may pose operational problems along the gas delivery system. Challenges of developing such a gas mixture quality monitoring program include: 1. challenges related to the appropriate kind of detection equipment and system required, 2. appropriate sampling system techniques, and 3. characterization of C6+ fractions if a gas chromatograph (GC) based system is used.

Current techniques for gas quality management for gas mixtures in the dense-phase include: a) Near-Infrared (NIR) methods, b) condensate collection methods, and c) methods based on analysis of gas composition and use of an appropriate equation of state to determine the cricondentherm.

NIR spectroscopy has been used in remote sensing and in hostile environments. The concept is based on the Lambert-Beer law for absorption of NIR radiation. The absorbance is linearly proportional to the path length of a specific component in the gas mixture and its respective concentration in the mixture. However, typical NIR methods suffer from the drawback of not being able to distinguish between C3-C5 components. Typical NIR methods also cannot determine nitrogen concentration in the gas mixture, as nitrogen does not have absorption bands. NIR systems are also by and large expensive and typically require an extensive calibration program. As well, this method typically cannot be used for on-line measurements.

The condensate collection method is based on the determination of the quality of condensate formed at a certain pre-selected pressure and temperature, which may be agreed upon between the supplier and the buyer. The basis of this method is that the gas mixture is allowed to cool through an isobaric, adiabatic or isothermic process, and the condensates formed are collected and measured by weight against the sample flow. This method can be used on-line. However, careful weighing of the collected condensate is key in achieving good results, and the setup is typically elaborate and expensive.

Methods based on compete analysis of gas composition, for example using a GC, requires an appropriate equation of state to determine the cricondentherm. Unfortunately, equations of state often have inherent uncertainties in calculating the dewpoint, and results may vary depending on the equation of state or equation parameters used. Such methods also face the problem of proper sampling as NGL (i.e., the heavier components) will most likely be dropped out in the sample stream to the gas analyzer. In fact, most industrial GCs only analyze to C6, the heavier components being typically assumed. The drawback is that the dewpoint is heavily influenced by small (e.g., ppm) levels of the heavier components which may not be analyzed by the GC. Typically, the real cricondentherm is at a warmer temperature than that calculated via composition from a GC. The result is that the gas may be richer than thought and as a consequence there may be unwanted liquids formed. Typically, the accuracy required for the GC-EOS method to be accurate is to determine each of the C6+ components to better than 10 ppm. Current GC technologies under field conditions require significant capital and maintenance in a C9+ analyzer and sampling system to achieve this.

It would be desirable to provide a method and system for monitoring gas mixtures that can be used for gas mixtures in the dense-phase region that addresses some of these challenges.

SUMMARY OF THE INVENTION

In some aspects, there is provided a method for monitoring quality of a given gas mixture being transmitted under pressure, the method comprising the steps of: throttling a sample of the gas mixture to a representative pressure; and measuring the hydrocarbon dew point of the sample at the representative pressure, the measured hydrocarbon dew point being indicative of the cricondentherm of the gas mixture; wherein the representative pressure is pre-selected to provide a pre-selected margin of error between measured hydrocarbon dew points of a set of representative gas mixtures at the representative pressure and respective cricondentherms of the set of representative gas mixtures, the representative gas mixtures being designed to have components representative of expected components of the given gas mixture.

The representative pressure may be pre-selected using a statistical method based on temperature-pressure relationships of the representative gas mixtures. The statistical method may comprise the steps of: calculating the temperature-pressure relationships of each of the representative gas mixtures; determining the cricondentherms of each of the representative gas mixtures using each respective temperature-pressure relationships; determining an optimal pressure corresponding to a maximum number of cricondentherms of the representative gas mixtures, within the pre-selected margin of error; and choosing the optimal pressure as the representative pressure.

In some aspects, there is provided a system for monitoring quality of a given gas mixture being transmitted under pressure, the system comprising: a throttler for throttling a sample of the gas mixture to a representative pressure; and a hydrocarbon dew point analyzer receiving the throttled sample from the throttler, the hydrocarbon dew point analyzer for measuring the hydrocarbon dew point of the sample at the representative pressure; wherein the representative pressure is pre-selected to provide a pre-selected margin of error between measured hydrocarbon dew points of a set of representative gas mixtures at the representative pressure and respective cricondentherms of the set of representative gas mixtures, the representative gas mixtures being designed to have components representative of expected components of the given gas mixture.

The representative pressure may be pre-selected using a statistical method based on temperature-pressure relationships of the representative gas mixtures. The representative pressure may be pre-selected based on determinations of the cricondentherms of the representative gas mixtures using calculated temperature-pressure relationships of each of the representative gas mixtures, the representative pressure being pre-selected to correspond to a maximum number of the determined cricondentherms, within the pre-selected margin of error.

In some aspects, the method and/or system described above may be used where the given gas mixture is being monitored at a natural gas plant or a natural gas distribution centre.

BRIEF DESCRIPTION OF THE DRAWINGS

Aspects of the present invention will be discussed in detail below, with reference to the drawings in which.

DETAILED DESCRIPTION OF THE INVENTION

All examples and embodiments discussed in the present application are for purposes of illustration only and are not intended to be limiting.

The present application presents a method and system for analyzing gas mixtures based on an estimate of the cricondentherm of the mixture. The method and system may be used for monitoring of gas mixtures in the dense-phase region. The method and system may be used for on-line monitoring of gas pipelines, and may be reliable and inexpensive compared to other current methods and systems.

The method and system is based on measuring the HCDP of a gas mixture at a representative pressure that has been selected to give results acceptably close to the cricondentherm for most gas mixtures. The gas mixture is brought to a pre-selected and constant representative pressure (Po) and then passed through an HCDP analyzer to determine the HCDP temperature at this pre-selected pressure. The determined HCDP temperature is then used to monitor the quality of the gas mixture, similar to monitoring based on the cricondentherm of the gas mixture. The premise is that the measured HCDP temperature at this representative pressure Po is close enough to the actual cricondentherm to be indicative of the richness of the gas mixture.

While this method and system may be particularly useful for dense-phase gas pipelines, they are also applicable to pipelines operating in other regions. For a dense-phase gas mixture, the gas mixture is throttled down to the pre-selected Po. For conventional gas mixtures, where the pressure of the gas may be less than that of a dense-phase gas, the pressure of the gas mixture is first increased, then brought down to Po. This method and system may be useful for gas mixture monitoring at different stages of the gas transmission system, including at the originating gas plant, and at local distribution companies.

The method and system may be based on a conventional real-time HCDP analyzer or manually with a Standard Bureau of Mines Dewpoint Tester. The method and system of this application may be implemented using standard off-the-shelf components currently used for gas monitoring.

Figure 1:
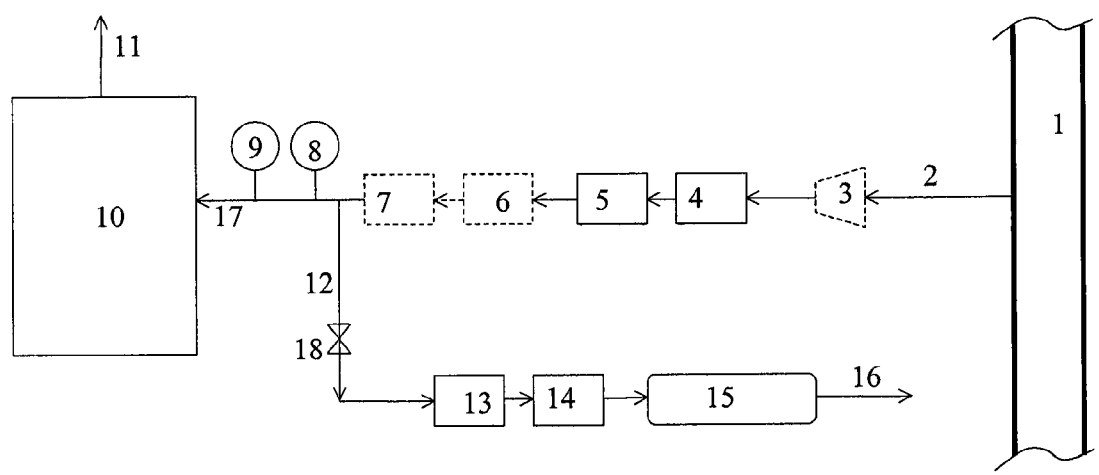
FIG. 1 is a block diagram illustrating a device for monitoring gas mixture quality.

Referring now to the drawings for purposes of the describing the method and system disclosed herein, FIG. 1 is a block diagram illustrating the components of an example monitoring system for a gas source 1. While the system and method is described with reference to monitoring a gas mixture at a gas source, it will be understood that the system and method may be adapted to monitoring at different steps along the gas distribution chain.

A gas sample stream 2 from the gas source 1 is drawn off for monitoring. The sample stream 2 may be relatively small compared to the pipeline. The sample stream 2 is then throttled to the representative pressure, Po. This may be done by first preheating the sample stream 2 using a pre-heater 4 and then throttling the sample stream 2 through a throttler, such as a pressure regulator 5, to the pre-selected Po. The throttler may alternatively be a constriction element, such as an orifice, or a porous element. Other suitable throttling methods may be used. If the set of pre-heater 4 and pressure regulator 5 is not sufficient to throttle the sample stream 2 to the pre-selected Po (e.g., where the pre-heater is insufficient to bring the gas mixture to the required pre-heating temperature before throttling), an additional set of a pre-heater 6 and a throttler, such as another pressure regulator 7, may be added in tandem as shown.

The pressure of the throttled stream 17 may be measured by a pressure transducer 8. A temperature transducer 9 may be used to measure the temperature of the throttled stream 17. The throttled stream 17 may be kept at a temperature above the expected HCDP of the gas at Po, for example at least 20° C. above the expected HCDP. Maintaining the temperature above the expected HCDP allows the HCDP analyzer 10 to start analysis with a clean (i.e., dew-free) mirror and to bring down the temperature in a controlled manner until the dew point is reached.

The HCDP of the throttled stream 17 is then measured, for example by an automated HCDP analyzer 10. The HCDP analyzer 10 may continuously log the measured HCDP data and may store the data in a memory. If analysis of the gas sample finds that the HCDP is outside of the expected or pre-determined specifications, the HCDP analyzer may set off an alarm or otherwise make a note of this discrepancy. The HCDP analyzer 10, after analyzing the throttled stream 17, may vent the gas out to atmosphere through a vent 11 or the gas may be returned to a utility gas stream (not shown) for use in heating.

The above-described system and method is applicable where the gas source 1 is at a pressure suitably greater than Po. Where the gas source 1 is at a pressure below Po or not suitably greater than Po, a compressor 3 may be added before the first pre-heater 4 to bring the sample stream 2 to a pressure suitably greater than Po. The compressor 3 may be relatively small.

The system may also provide the ability to draw off gas samples for more thorough analysis, for example for the purpose of ongoing validation of Po. In the example shown, a side stream 12 may be extracted through a valve 18 for further analysis. This extraction may be performed at fixed intervals, for example every few weeks, by an operator on-site. This side stream 12 may then be throttled to slightly above ambient pressure using a pre-heater 13 and a throttler, such as a pressure regulator 14. The throttled side stream may then be collected in a collection vessel, for example a charcoal sample bottle 15, before being vented to the atmosphere through vent 16. The collected sample may then be disconnected and sent to a lab for further analysis. Such further analysis may be used for verification of the HCDP measurements.

The system may also be modular, meaning that individual components of the system may be independently removed or added. This allows each component to be separately modified, removed, or added as necessary for a specific application. The system may also be mobile. This allows a single system to monitor gas mixture quality at different points in the gas distribution system. A mobile embodiment of the system may be in the form of a monitoring vehicle, or the system may be made portable.

Selection of the components of this system would be clear to a person skilled in the art. Typically, these components are similar to those currently used in gas monitoring systems.

Figure 2:
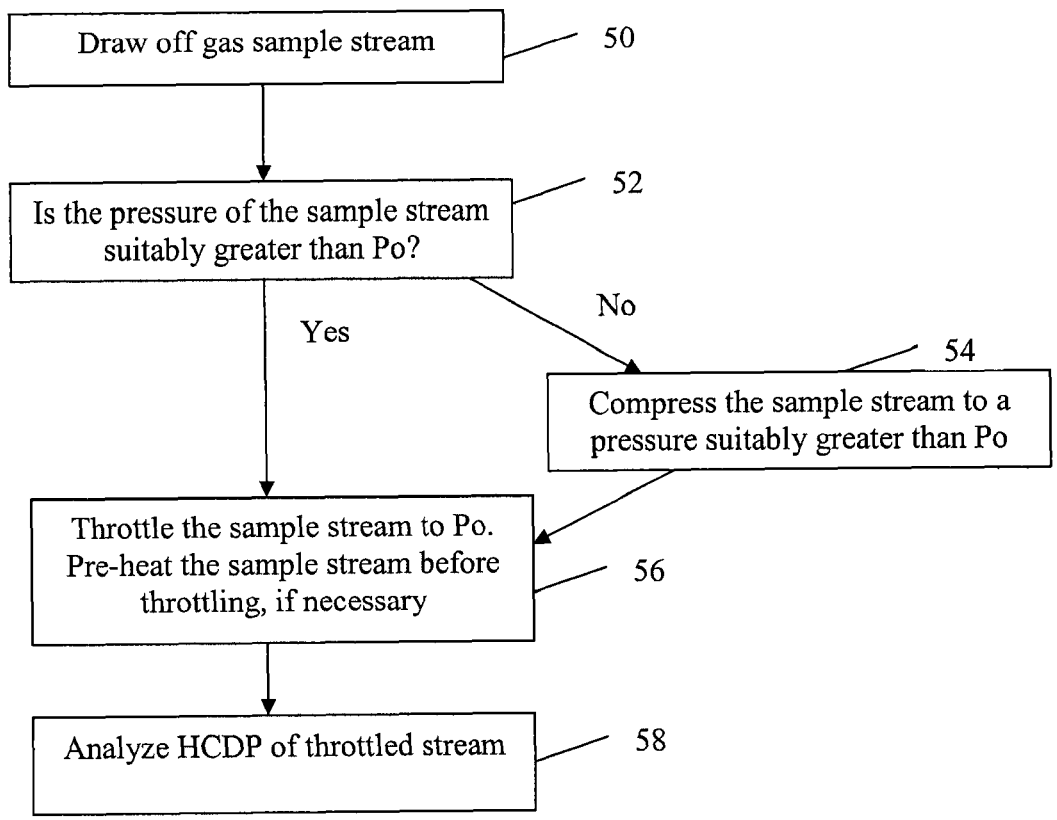
FIG. 2 is a flowchart illustrating a method for monitoring gas mixture quality.

FIG. 2 illustrates a method of monitoring gas mixture quality. This method is based on using a pre-selected reference pressure Po as an estimate for the cricondentherm, as described above.

At a step 50, a gas sample stream is drawn off for analysis and monitoring.

At a step 52, it is necessary to know whether the sample stream is at a pressure suitably greater than Po. Having the sample stream at a suitably high pressure allows the sample stream to be properly throttled to Po.

If the pressure is not suitably greater than Po, then at a step 54, the sample stream is compressed until it has a pressure suitably greater than Po. This may be performed by a standard compressor.

At a step 56, the sample stream is at a pressure suitably greater than Po. The sample stream is throttled to the pre-selected Po. The sample stream may be pre-heated prior to throttling. This throttling may take place over multiple pre-heating and throttling stages.

At a step 58, the throttled stream is analyzed, and the HCDP of the gas mixture at Po is determined. The throttled stream may be maintained at a temperature greater than the expected HCDP prior to analysis. The pressure and/or temperature of the throttled stream may be monitored prior to analysis to ensure that the throttled stream is maintained at the desired pressure and/or temperature. After analysis, any remaining sample gas may be vented to atmosphere.

The method described above is only an example of the method of monitoring gas mixture quality, and is not intended to be limiting.

Selection of Representative Pressure

One aspect of the present method and system is a representative pressure Po that results in a measured HCDP that is acceptably close to the actual cricondentherm. What is considered an acceptable HCDP may be dependent on the specific application. A Po for an acceptable HCDP measurement may be chosen based on a certain percentage of gas mixtures having a cricondentherm that falls within a certain error margin of the measured HCDP at Po. It has been found that a statistical method may be suitable for selecting Po. Such a statistical method is described here, but other methods of selecting Po may be possible.

Figure 3:
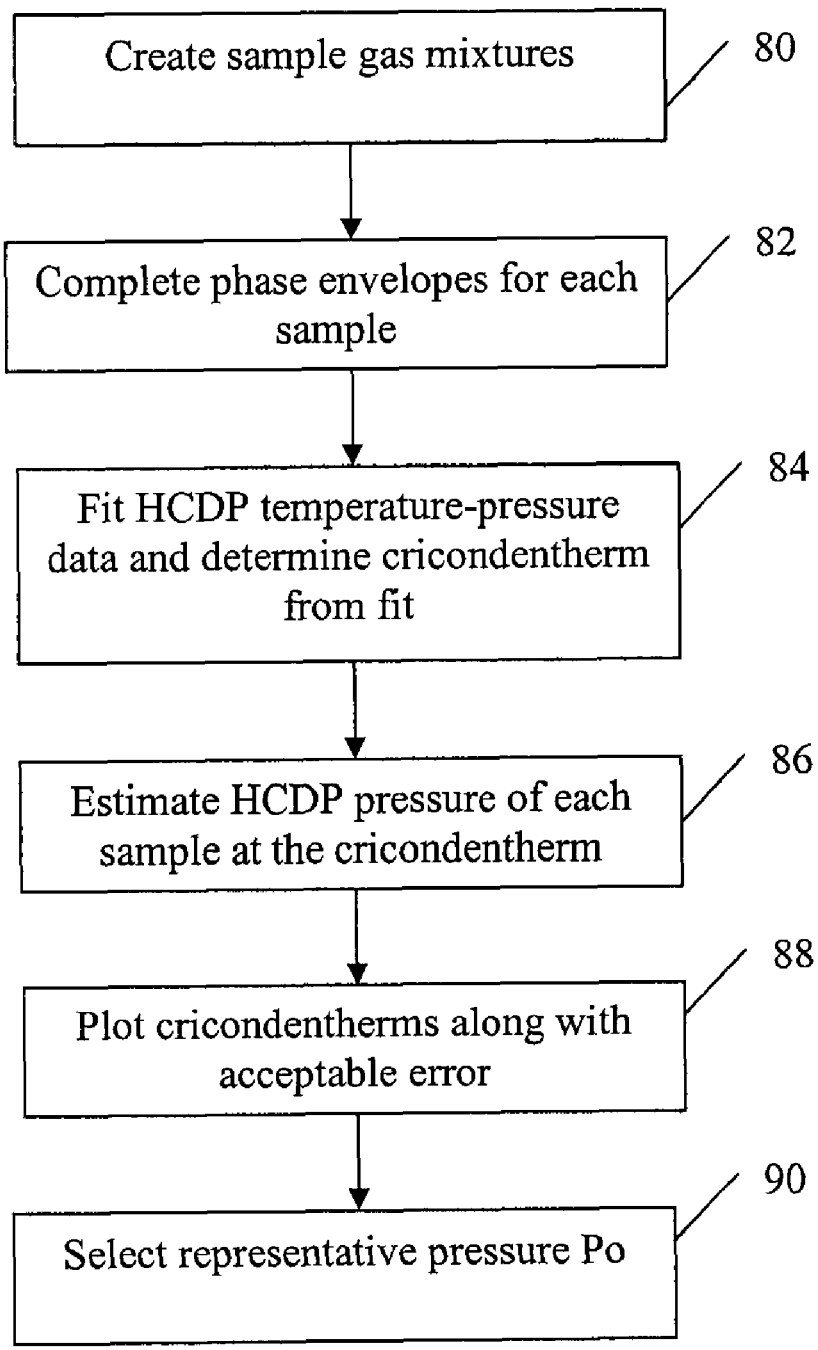
FIG. 3 is a flowchart illustrating a statistic-based method for selecting a representative pressure Po.

FIG. 3 illustrates an example of a suitable statistical method for selecting Po in the form of a flowchart. The result of this method may be improved by selecting a greater number of samples and wider lower and upper bounds for each component in the samples. Another way to improve the result may be by performing real gas sampling on individual gas streams of interest and narrowing the component upper and lower bounds to a narrower range, in order to obtain a more precise result for the specific case of interest.

1. At a step 80, samples of gas mixtures are prepared. The proportions of each component in the mixture may be based on the upper and lower bounds typically found in natural gas. These samples may exhaustively cover all combinations of upper and lower bounds, or may only be a selection of upper and/or lower bounds. As discussed above, selection of the upper and lower bounds may affect the results of this method.

2. At a step 82, the phase envelopes for each mixture is completed, for example using an appropriate equation of state (EOS). A possible EOS is Peng-Robinson with Huron-Vidal mixing rules (PR-MHV). Other EOS known in the art may be used, for example Redlich Kwon and its derivatives, AGA-8, and GERG. Other methods for completing the phase envelopes may also be used. It has been found that using an EOS to determine the pressure of the cricondentherm is associated with less error than using an EOS to directly determine the temperature of the cricondentherm.

3. At a step 84, the HCDP pressure vs. temperature data for each sample is fitted into a polynomial, such as a fourth-order polynomial, and the cricondentherm was determined based on this fit. Other fits are possible, for example a spline, inverse polynomial, and power function. Determination of the cricondentherm may be based on calculating the maximum of the temperature-pressure graph (i.e., where $dT/dP=0$).

4. At a step 86, the HCDP pressure for each mixture at the cricondentherm is estimated. The upper and lower bounds for the pressure may be also estimated, based on a certain error margin for the cricondentherm, such as 1° C. This error margin may be dependent on industry standards, and may be larger or smaller dependent on the specific application. Typically, a 2° C. error margin is considered acceptable, based on the current measurement technology.

5. At a step 88, the determined cricondentherms for all of the mixtures are plotted on a pressure-temperature diagram, along with the corresponding upper and lower bounds of the HCDP pressure at temperatures corresponding to the respective cricondentherm minus 1° C.

6. At a step 90, a pressure Po is selected such that the maximum number of gas mixture samples have a cricondentherm (within the specified error margin) occurring at Po.

Similar calculations may be made for other pressure bounds, depending on the error tolerance that is acceptable, e.g., 0.5° C., 2° C., or 3° C. For different error margins, the selected pressure Po may be different. As such, the above-described method may be repeated if the desired error margin is changed. Alternatively, the above-described method may be performed once for a number of different error margins, and the pressure-temperature diagram created in step 6 may include information for these different error margins, such that the representative pressure Po can be selected from this diagram without having to repeat steps 1-6 every time.

EXAMPLE

In one non-limiting example, the statistical method for selecting Po may be based on the upper and lower bounds of hydrocarbon components found in typical industrial gas mixtures. The samples used to determine Po may exhaustively cover all such upper and lower bounds. An example of typical upper and lower bounds found in industrial natural gas mixtures is provided in Table 1.

TABLE 1

| Component | Lower Bound (mole %) | Upper Bound (mole %) |
|---|---|---|
| hydrogen | 0.01 | 0.01 |
| nitrogen | 0 | 1.5 |
| carbon dioxide | 0 | 0.7 |
| methane | 81 | 97 |
| ethane | 2.94 | 10 |
| propane | 0.1902 | 4 |
| i-butane | 0.0156 | 1 |
| n-butane | 0.0253 | 1 |
| i-pentane | 0.0041 | 0.1 |
| n-pentane | 0.003 | 0.1 |
| n-hexane | 0.0013 | 0.08 |
| n-heptane | 0 | 0.04 |
| n-octane | 0 | 0.03 |
| n-nonane | 0 | 0.02 |

Based on these industry standards, 1024 gas mixtures were created, using the upper and lower bounds specified in Table 1.

Figure 4:
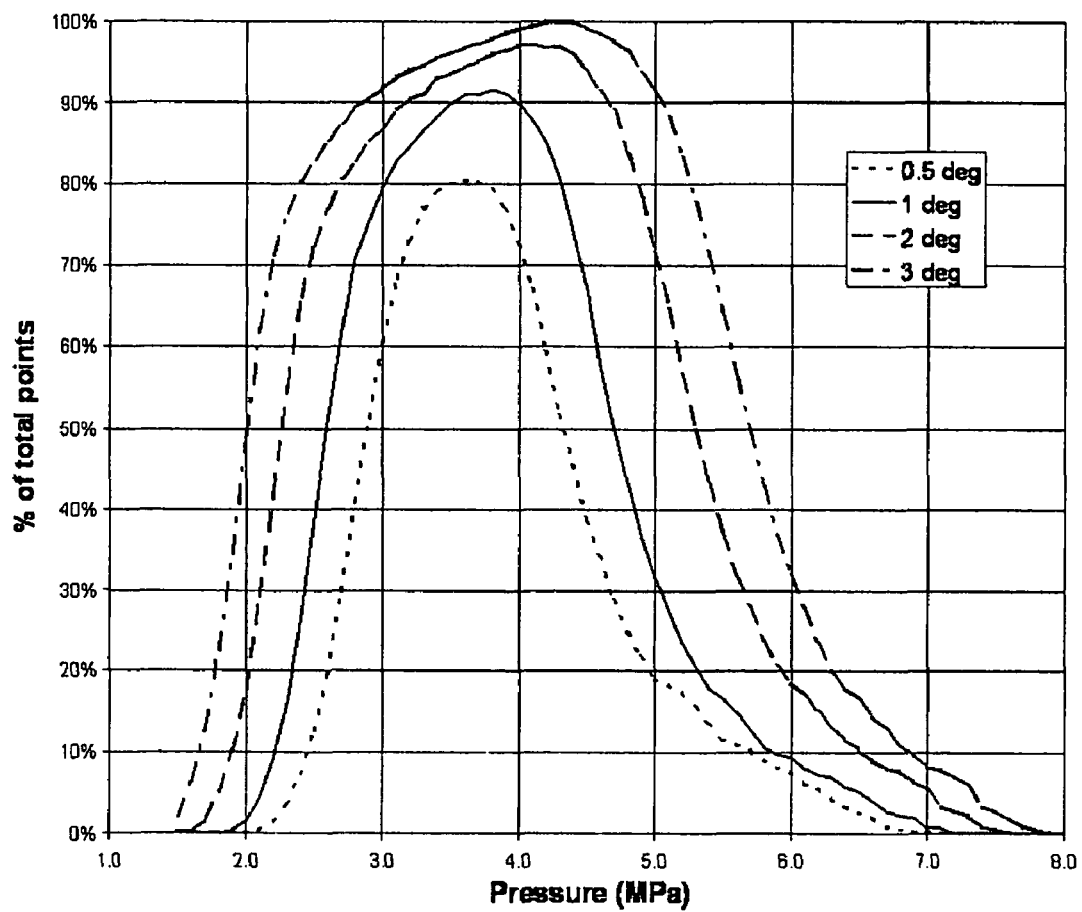
FIG. 4 is an example pressure-temperature diagram created using the method illustrated in FIG. 1.

The 1024 gas mixtures were used to create a pressure-temperature diagram using the statistical method described above. The phase envelope was completed for the gas mixtures using PR-MHV as the EOS, and the data was fitted to a fourth order polynomial. The resultant pressure-temperature diagram is shown in FIG. 4. The pressure-temperature diagrams are shown for error margins corresponding to a HCDP temperature deviation of 0.5° C., 1° C., 2° C., and 3° C. from the actual cricondentherm. From the diagram, it was found that 90% of the samples had a cricondentherm that fell into a 1° C. error margin when the HCDP was measured at a pressure of 3.8 MPa. Hence, for this particular example, the representative Po would be selected as 3.8 MPa.

The accuracy of the estimated cricondentherm at this Po was tested using 5 test samples. Table 2 describes the components of the 5 test samples. Some samples were purposely selected to have compositions outside the expected range for a natural gas (e.g., sample #3 has methane and ethane % outside of the expected upper and lower bounds) in order to test the robustness of this method.

TABLE 2

| | Samples | | | | |
|---|---|---|---|---|---|
| | Sample #1 | Sample #2 | Sample #3 | Sample #4 | Sample #5 |
| nitrogen | 0.6378 | 0.5490 | 0.4237 | 0.6378 | 0.6353 |
| carbon dioxide | 1.0290 | 1.0899 | 0.9573 | 0.9396 | 1.0238 |
| methane | 91.6906 | 79.9412 | 67.6470 | 89.3499 | 91.7989 |
| ethane | 4.7845 | 13.5074 | 22.9313 | 4.5860 | 4.6836 |
| propane | 1.3403 | 4.4206 | 7.6170 | 1.2175 | 1.3002 |
| i-butane | 0.1631 | 0.1587 | 0.1457 | 0.6197 | 0.1589 |
| n-butane | 0.2222 | 0.2030 | 0.1680 | 2.5306 | 0.2167 |
| i-pentane | 0.0543 | 0.0506 | 0.0437 | 0.0458 | 0.0547 |
| n-pentane | 0.0399 | 0.0373 | 0.0319 | 0.0337 | 0.0418 |
| C6fraction | 0.0230 | 0.0280 | 0.0226 | 0.0275 | 0.0158 |
| C7fraction | 0.0103 | 0.0111 | 0.0097 | 0.0095 | 0.0385 |
| C8fraction | 0.0045 | 0.0029 | 0.0019 | 0.0021 | 0.0276 |
| C9+ | 0.0005 | 0.0003 | 0.0004 | 0.0002 | 0.0041 |

The actual cricondentherms, arrived at using an EOS, of the five samples described in Table 2 were compared to the measured HCDP using the selected Po of 3.8 MPa. The results are given in Table 3. The differences between the measured HCDP and the actual cricondentherm are acceptably small, even for those sample having compositions outside of the expected range.

TABLE 3

| Sample | Measured HCDP at selected Po of 3.8 MPa (deg C.) | Expected cricondentherm from an Equation of State (deg C.) | Difference (deg C.) |
|---|---|---|---|
| Sample #1 | −16.6 | −10.5 | −6.1 |
| Sample #2 | −11.22 | −6.76 | −4.46 |
| Sample #3 | −1.13 | 0.86 | −1.99 |
| Sample #4 | −0.42 | 0.76 | −1.18 |
| Sample #5 | 9.96 | 11.54 | −1.58 |

Applications

The method and system described above may be used to monitor gas mixtures in the dense-phase region. Typically, at dense-phase operating pressures, traditional methods such as the condensate collection method are unable to determine the hydrocarbon content of the gas stream. The problem with dense-phase transportation is that operational issues may result downstream as pressures drop, whether it is in the transmission pipeline network or at end user levels. In some applications, the monitoring system may have pressure regulators and pre-heaters to ensure there is no liquid dropout.

The method and system may also be used to monitor gas mixtures at conventional operating pressures (i.e., below the dense-phase region). The same method and system could be used for the same reasons pertaining to ensuring liquids do not drop out. In such conventional applications, the sampling pressures may be boosted to above the representative pressure before being throttled down, and the sample may be cooled before analysis.

There may also be other uses up and down the natural gas energy chain. At the upstream side of things, this method and system may be used to ensure gas quality compliance and process performance at a gas plant level. At the downstream side, local distribution companies or industrials may perform a similar analysis which may be of use for operating, contract or compliance reasons. Although the above description has been with reference to certain embodiments and examples, a person skilled in the art would understand that variations to the method and system are possible.

What is claimed is:

1. A method for monitoring quality of a given gas mixture being transmitted under pressure, the method comprising the steps of:
   throttling a sample of the given gas mixture to a representative pressure;
   measuring the hydrocarbon dew point of the sample at the representative pressure, the measured hydrocarbon dew point being indicative of the cricondentherm of the given gas mixture; and
   monitoring the quality of the given gas mixture based on the hydrocarbon dew point indicative of the cricondentherm;
   wherein the representative pressure is pre-selected to provide a pre-selected margin of error between measured hydrocarbon dew points of a set of representative gas mixtures at the representative pressure and respective cricondentherms of the set of representative gas mixtures, the representative gas mixtures being designed to have components representative of expected components of the given gas mixture.

2. The method of claim 1 further comprising after the throttling step, maintaining the sample at a temperature greater than an expected hydrocarbon dew point of the given gas mixture before the measuring step.

3. The method of claim 1 further comprising the step of compressing the sample to a pressure greater than the representative pressure before the throttling step.

4. The method of claim 1 further comprising the step of storing the measured hydrocarbon dew point in a memory.

5. The method of claim 1 further comprising the step of comparing the measured hydrocarbon dew point to a pre-determined range and triggering a notification if the measured hydrocarbon dew point is outside of the pre-determined range.

6. The method of claim 1 wherein the given gas mixture is being monitored at one of: a natural gas plant and a natural gas distribution centre.

7. The method of claim 1 wherein the throttling step comprises pre-heating the sample to a throttling temperature greater than an expected hydrocarbon dew point and throttling the sample to the representative pressure.

8. The method of claim 7 wherein the throttling step comprises pre-heating the sample to an intermediate temperature and throttling the sample to an intermediate pressure before pre-heating the sample to the throttling temperature and throttling the sample to the representative pressure, the intermediate temperature being lower than the throttling temperature and the intermediate pressure being higher than the representative pressure.

9. The method of claim 1 wherein the representative pressure is pre-selected using a statistical method based on temperature-pressure relationships of the representative gas mixtures.

10. The method of claim 9 wherein the statistical method comprises the steps of:
calculating the temperature-pressure relationships of each of the representative gas mixtures;
determining the cricondentherms of each of the representative gas mixtures using each respective temperature-pressure relationships;
determining an optimal pressure corresponding to a maximum number of cricondentherms of the representative gas mixtures, within the pre-selected margin of error; and
choosing the optimal pressure as the representative pressure.

11. The method of claim 10 wherein the temperature-pressure relationships of each of the representative gas mixtures are calculated using an equation of state.

12. The method of claim 10 wherein the cricondentherms of each of the representative gas mixtures are determined by using a fit to the respective calculated temperature-pressure relationships of each of the representative gas mixtures.

13. The method of claim 12 wherein the fit is selected from the group consisting of: a polynomial fit, a spline fit, an inverse polynomial fit, and a power function fit.

14. The method of claim 13 wherein the polynomial fit is a fourth-order polynomial fit.

15. A system for monitoring quality of a given gas mixture being transmitted under pressure, the system comprising:
a throttler for throttling a sample of the gas mixture to a representative pressure; and
a hydrocarbon dew point analyzer receiving the throttled sample from the throttler, the hydrocarbon dew point analyzer for measuring the hydrocarbon dew point of the sample at the representative pressure;
wherein the representative pressure is pre-selected to provide a pre-selected margin of error between measured hydrocarbon dew points of a set of representative gas mixtures at the representative pressure and respective cricondentherms of the set of representative gas mixtures, the representative gas mixtures being designed to have components representative of expected components of the given gas mixture.

16. The system of claim 15 further comprising a pressure sensor and a temperature sensor for monitoring the pressure and temperature of the throttled sample.

17. The system of claim 15 wherein the hydrocarbon dew point analyzer has a memory for storing measured hydrocarbon dew points.

18. The system of claim 15 wherein the hydrocarbon dew point analyzer has a notification system that is triggered when a measured hydrocarbon dew point is outside a pre-determined range.

19. The system of claim 15 further comprising a pre-heater for pre-heating the sample to a throttling temperature greater than an expected hydrocarbon dew point, the pre-heater providing the pre-heated sample to the throttler.

20. The system of claim 19 further comprising an intermediate pre-heater for pre-heating the sample to an intermediate temperature and an intermediate throttler for throttling the sample to an intermediate pressure before providing the sample to the pre-heater, the intermediate temperature being lower than the throttling temperature and the intermediate pressure being higher than the representative pressure.

21. The system of claim 15 wherein the representative pressure is pre-selected using a statistical method based on temperature-pressure relationships of the representative gas mixtures.

22. The system of claim 21 wherein the representative pressure is pre-selected based on determinations of the cricondentherms of the representative gas mixtures using calculated temperature-pressure relationships of each of the representative gas mixtures, the representative pressure being pre-selected to correspond to a maximum number of the determined cricondentherms, within the pre-selected margin of error.

23. The system of claim 22 wherein the temperature-pressure relationships of each of the representative gas mixtures are calculated using an equation of state.

24. The system of claim 22 wherein the cricondentherms of each of the representative gas mixtures are determined by using a fit to the respective calculated temperature-pressure relationships of each of the representative gas mixtures.

25. The system of claim 24 wherein the fit is selected from the group consisting of: a polynomial fit, a spline fit, an inverse polynomial fit, and a power function fit.

* * * * *